US006946446B2

(12) United States Patent
Ma et al.

(10) Patent No.: US 6,946,446 B2
(45) Date of Patent: Sep. 20, 2005

(54) ANTI-INFECTIVE AGENTS USEFUL AGAINST MULTIDRUG-RESISTANT STRAINS OF BACTERIA

(75) Inventors: Zhenkun Ma, Gurnee, IL (US); Peter Nemoto, Danbury, CT (US); Suoming Zhang, Gainesville, FL (US); Hong Yong, Grayslake, IL (US); Yat Sun Or, Cambridge, MA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/791,408

(22) Filed: Feb. 23, 2001

(65) Prior Publication Data

US 2002/0019355 A1 Feb. 14, 2002

Related U.S. Application Data

(60) Provisional application No. 60/184,622, filed on Feb. 24, 2000.

(51) Int. Cl.$^7$ ............................................. A01N 43/04
(52) U.S. Cl. .......................... 514/29; 536/7.3; 536/7.4
(58) Field of Search ............................ 514/29; 536/7.3, 536/7.4

(56) References Cited

U.S. PATENT DOCUMENTS

| 4,331,803 | A | 5/1982 | Watanabe et al. ............ 536/7.2 |
| 4,670,549 | A | 6/1987 | Morimoto et al. |
| 4,680,368 | A | 7/1987 | Nakamoto et al. |
| 4,990,602 | A | 2/1991 | Morimoto et al. |
| 5,523,399 | A | 6/1996 | Asaka et al. |
| 5,631,355 | A | 5/1997 | Asaka et al. |
| 5,770,579 | A | 6/1998 | Agouridas et al. |
| 5,866,549 | A | 2/1999 | Or et al. |
| 6,075,011 | A | 6/2000 | Or et al. |

FOREIGN PATENT DOCUMENTS

| EP | 0194833 | 9/1986 |
| EP | 0260938 A2 | 3/1988 |
| EP | 0487411 | 5/1992 |
| EP | 0680967 A1 | 11/1995 |
| EP | 1167375 | 1/2002 |
| FR | 2732023 | 9/1996 |
| FR | 2732032 | 9/1996 |
| WO | 9742204 | 11/1997 |
| WO | 9856800 | 12/1998 |
| WO | WO 98/56800 | 12/1998 |
| WO | 0061593 | 10/1999 |

OTHER PUBLICATIONS

Schempp et al, "Antibacterial activity of hyperforin from St John's wort, against multiresistant *Staphylococcus aureus* and gram–positive bacteria", 353, No. 9170 (1999), p. 2129.

Agouridas et al, "Synthesis and antibacterial activity of Ketolides (6–0–Methyl–3–Oxoerythromycin Derivatives): A New Class of Antibaterials Highly Potent Against Macrolide–Resistant and Susceptible Respiratory Pathyogens", Journal of Medicinal Chemistry, American Chemical Society, 21 (41), 4080–4100 (1998).

Bertho, et al., "Solution conformation of methylated macrolide antibiotics roxithromycin and erythromycin using NMR and molecular modeling. Ribosome–bound conformation determined by TRNOE and formulation of cytochrome P450–metabolite complex", International Journal of Biological Macromolecules (1998), 22(2), 103–127.

Derwent Publications Ltd, London, XP002219408, "New erythromycin derivatives are antimicrobial agents active e.g. Mycobacterium avium complex".

Y. Kawashima et al., *Structure–Activity Relationship Study of 6–O–Methylerythromycin 9–O Substituted oxime Derivatives*, Chem. Pharm. Bull., 42(5):1088–1095 (1994).

J.J. Schentag, et al., "Genesis of Methicillin–Resistant *Staphylococcus aureus* (MRSA). How Treatment of MRSA Infections Has Selected for Vancomycin– Resistant *Enterococcus faecium*, and the Importance of Antibiotic Management and Infection Control", Clinical Infectious Diseases, 26; 1204–14 (1998).

F. Baquero, et al., "Gram–positive resistance: challenge for the development of new antibiotics", Journal of Antimicrobial Chemotherapy, 39; Suppl. A, 1–6 (1997).

Y. Kawashima et al., "Structure–Activity Relationship Study of 6–O–Methylerythromycin 9–O–Substituted Oxime Derivatives", Chem. Pharm. Bull, vol. 42 No. 5, pp.1088–1095 (1994).

*Primary Examiner*—Elli Peselev
(74) *Attorney, Agent, or Firm*—B. Coregory Donner

(57) ABSTRACT

The invention relates to novel methods for using macrolide anti-infective agents. The macrolide anti-infective agents demonstrate antibacterial activity against multi-drug resistant strains of bacteria and, in particular, methicillin-resistant *Staphylococcus aureus* (MRSA). Methods for inhibiting the activity of multi-drug resistant bacterial organisms and methods for treating a bacterial infection caused by such organisms are described herein.

20 Claims, No Drawings

ANTI-INFECTIVE AGENTS USEFUL AGAINST MULTIDRUG-RESISTANT STRAINS OF BACTERIA

This application claims the benefit of U.S. Provisional Application No. 60/184,622 filed Feb. 24, 2000.

TECHNICAL FIELD

The invention relates to novel methods for using macrolide anti-infective agents. The macrolide anti-infective agents demonstrate antibacterial activity against multi-drug resistant strains of bacteria and, in particular, methicillin-resistant staphylococci. Methods for inhibiting the activity of multi-drug resistant bacterial organisms and methods for treating a bacterial infection caused by such organisms are described herein.

BACKGROUND OF THE INVENTION

Macrolide antibiotics are commonly used antibacterial agents. For over four decades, macrolide compounds have been used as safe and effective antibacterial agents against a wide spectrum of bacterial organisms. The macrolide compounds generally demonstrate activity against a wide spectrum of bacterial organisms. Erythromycins A, B, C and D having the formula:

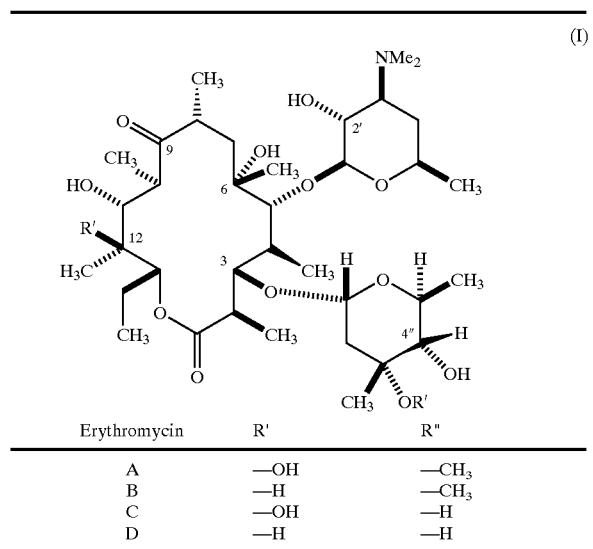

| Erythromycin | R' | R" |
|---|---|---|
| A | —OH | —CH$_3$ |
| B | —H | —CH$_3$ |
| C | —OH | —H |
| D | —H | —H | are well-known and potent antibacterial agents, which have been widely used to treat and prevent bacterial infection. Erythromycin compounds are only a few of the macrocyclic antibacterial agents currently in use in the clinical setting. Clarithromycin, for example, is a 6-O-methylerythromycin A derivative, which has demonstrated antibacterial activity against a broad spectrum of bacterial organisms. See, for example, U.S. Pat. No. 4,331,803. Another common anti-infective agent, azithromycin, differs chemically from erythromycin in that a methyl-substituted nitrogen atom is incorporated into the lactone ring.

The extensive clinical application of these antibiotic agents has resulted in an increasing emergence of macrolide-resistant strains of bacteria. The medical need for effective agents against resistant organisms, including staphylococci, streptococci and enterococci, has grown as a result of the ever-increasing resistance of the organisms. See, *Journal of Antimicrobial Chemotherapy* 39, Suppl. A, 1–6 (1997) and *Clinical Infectious Diseases* 26: 1204–14 (1998).

Ongoing efforts to develop compounds demonstrating activity against the resistant organisms have resulted in a number of new macrolide series. The compounds have been described in the following U.S. patents.

U.S. Pat. No. 5,523,399 describes a class of 5-desosaminylerythronolide derivatives, wherein a carbamoyl group is introduced into the 3-position of the lactone ring. See also U.S. Pat. No. 5,631,355, disclosing 5-desosaminylerythronolide derivatives having a 9,11-bridged cyclic imine group. There is no report of antibacterial activity against a methicillin-resistant strain of *Staphylococcus aureus* (MRSA).

U.S. Pat. No. 5,770,579 describes a class of 6-O-methylerythromycin, 9-oxime derivatives having antibacterial activity. No activity against MRSA was reported. See also European Patent Publication No. 0 680 967 A1 and French Publication No. 2,732,032 A1.

PCT International Application No. PCT/IB98/00741 relates to a class of 6-O-methyl-9-oxime ketolides which are useful for the treatment of bacterial and protozoal infections. There is no description that the compounds demonstrate activity in inhibiting the bacterial activity of MRSA.

In Chem. Pharm. Bull. 42(5), 1088–1095, 1994, 6-O-methylerythromycin 9-O-substituted oxime derivatives exhibiting activity against erythromycin-resistant *Staph. aureus* was described. There is no report of antibacterial activity against the MRSA.

The cited compounds are erythromycin derivatives or ketolide derivatives, i.e. wherein the cladinose sugar of the erythromycin is removed. None of the previously cited compounds have a substituent in the 6-O-position other than methyl. U.S. patent application Ser. No. 08/841,038 and U.S. Pat. No. 5,866,549 describe 6-O-substituted erythromycin and ketolide derivatives, respectively, wherein the 6-O-substituent can be other than methyl. Although 9-oxime groups on the 6-O-substituted ketolides was disclosed in U.S. Pat. No. 5,866,549, no activity against MRSA was reported.

The 9-oxime derivatives of erythromycin generally have been described as intermediates for the preparation of macrolide compounds currently in clinical use. However, there has been some recognition that 9-oxime derivatives of erythromycin can have antibacterial activity; see for example U.S. Pat. No. 5,770,579; European Patent Publication No. 0 680 967 A1; French Publication No. 2,732,032 A1; and PCT International Application No. PCT/IB98/00741. There is no recognition or appreciation that macrolide compounds can demonstrate activity against methicillin-resistant strains of staphylococci or that administering a macrolide compound can treat a bacterial infection caused by such MRSA.

Accordingly, there remains a need to identify and develop new classes of macrocylic compounds demonstrating antibacterial activity against an increasing number of multi-drug, methicillin-resistant strains of bacteria. The new classes of macrocyclic compounds can be erythromycin derivatives or ketolide derivatives. A useful drug would demonstrate activity against multi-drug resistant strains of bacteria, in particular MRSA.

SUMMARY OF THE INVENTION

In one aspect, the invention relates to a method for inhibiting the activity of a methicillin-resistant strain of staphylococci. The method comprises administering an effective amount of a macrolide compound demonstrating activity in inhibiting the activity of methicillin-resistant bacteria. The compounds administered in the method are erythromycin derivatives having a 9-oxime functionality and the 6-O-position substituted with a saturated or unsaturated hydrocarbon optionally substituted with a halogen, heteroatom, aromatic group, heterocycle, or a carbonyl, sulfonyl, or amino functional group. The 6-O-substituted 9-oxime erythromycin derivatives inhibit the activity of multi-drug resistant strains of bacteria, particularly MRSA.

In another aspect, the invention relates to a method for treating a bacterial infection caused by MRSA in a mammal. The compounds have demonstrated activity in vitro for inhibiting the bacterial activity of the Staph. aureus.

In yet another aspect, the invention relates to novel compounds useful for the method of the invention. The compounds are 6-O-substituted 9-oxime erythromycin derivatives, which can exhibit activity for inhibiting multi-drug resistant strains of bacteria, such as MRSA.

DETAILED DESCRIPTION OF THE INVENTION

In a first aspect, the invention comprises applying an effective amount of a 9-oxime-6-O-substituted erythromycin derivative to a resistant strain of bacteria. The method demonstrates effectiveness for inhibiting the bacterial activity of MRSA. In this aspect of the invention, the compound can be applied in any suitable manner for commingling the desired compound with the bacteria.

Compounds suitable for the invention can have a general formula (I), (II) or (III), below:

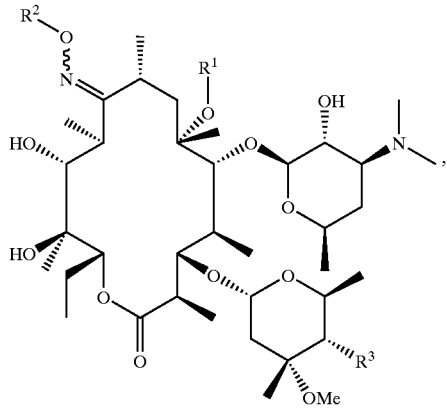

I

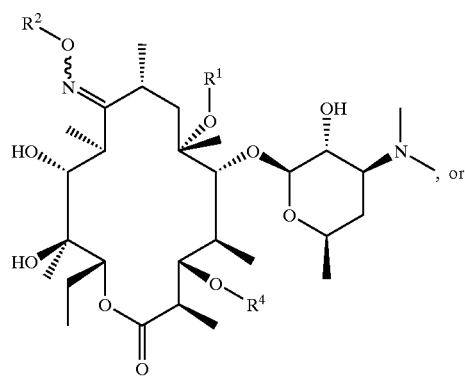

II

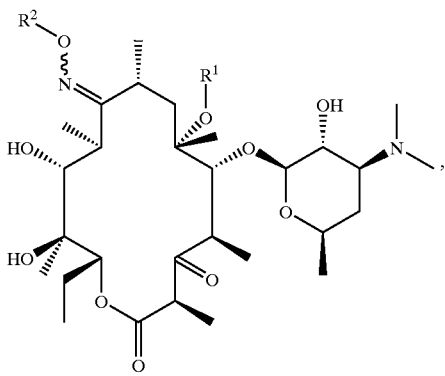

III wherein:

$R^1$ is selected from the group consisting of:
   a hydrocarbon selected from the group consisting of $C_1$–$C_{12}$ alkyl, $C_3$–$C_{12}$ alkenyl, wherein 1 to 3 carbons of said hydrocarbon is optionally replaced by an O, S or N heteroatom, or a group selected from —C(O)—, —C=N—, —C=N—O— and —N($R^5$)—; and wherein said hydrocarbon is optionally substituted with one to three substituents selected from —C(O)$R^6$, —S(O)$_n$$R^6$, —NHC(O)N$R^6$, —NHC(O)N$R^7$$R^8$, halogen, aryl, substituted aryl, heteroaryl, substituted heteroaryl and heterocycloalkyl, wherein n is 1 or 2;

$R^2$ is selected from the group consisting of:
   a. hydrogen,
   b. a hydrocarbon selected from the group consisting of $C_1$–$C_{12}$ alkyl, $C_3$–$C_{12}$ alkenyl, and $C_3$–$C_{12}$ alkynyl, wherein 1 to 3 carbons of said hydrocarbon is optionally replaced by an O, S or N heteroatom, or a group selected from —C(O)—, —C=N—, —C=N—O— and —N($R^5$)—; and wherein said hydrocarbon is optionally substituted with one to three substituents selected from —C(O)$R^6$, —S(O)$_n$$R^6$, —NHC(O)$R^6$, —NHC(O)N$R^7$$R^8$, halogen, aryl, substituted aryl, heteroaryl, substituted heteroaryl and heterocycloalkyl;
   c. optionally substituted aryl; and
   d. optionally substituted heteroaryl;

$R^3$ is selected from the group consisting of:
   a. —H,
   b. —OH,
   c. —OC(O)$R^9$,
   d. —OC(O)NH$R^9$, and
   e. —OC(O)O$R^9$;

$R^4$ is selected from the group consisting of:
   a. —H,
   b. —C(O)$R^9$,
   c. —C(O)NH$R^9$, and
   d. —C(O)O$R^9$;

$R^5$ is hydrogen, $C_1$–$C_6$ alkyl, $C_1$–$C_6$ alkyl substituted with optionally substituted aryl or optionally substituted heteroaryl, optionally substituted aryl, or optionally substituted heteroaryl;

$R^6$ is hydrogen, alkyl optionally substituted with aryl or heteroaryl, optionally substituted aryl, optionally substituted heteroaryl;

$R^7$ and $R^8$ are independently selected from the group consisting of hydrogen, $C_1$–$C_6$ alkyl, $C_1$–$C_6$ alkyl substituted with optionally substituted aryl or heteroaryl, optionally substituted aryl, or optionally substituted heteroaryl, or $R^7$ and $R^8$ taken together with the atoms to which they are attached form a $C_3$–$C_{12}$ cycloalkyl group; and $R^9$ is a hydrocarbon selected from the group consisting of $C_1$–$C_{12}$ alkyl, $C_3$–$C_{12}$ alkenyl, and $C_3$–$C_{12}$ alkynyl, wherein 1 to 3 carbons of said hydrocarbon are optionally replaced by an O, S or N heteroatom, or a group selected from —C(O)—, —C=N—, —C=N—O— and —N($R^5$)—; and wherein said hydrocarbon is optionally substituted with one to three substituents selected from —C(O)$R^6$, —S(O)$_n R^6$, —NHC(O)$R^6$, —NHC(O)N$R^7 R^8$, halogen, aryl, substituted aryl, heteroaryl, substituted heteroaryl and heterocycloalkyl.

For the convenience of the reader, certain terms used to describe the compounds administered by the invention herein are defined below.

The terms "$C_1$–$C_{12}$ alkyl" as used herein refer to a saturated, straight, or branched chain monovalent group derived from a hydrocarbon moiety comprising one to twelve carbon atoms by removal of a single hydrogen atom. In general, a group denoted as $C_x$–$C_y$, wherein x and y are integers, refers to the identified parent group having from x to y carbon atoms. For example, the group $C_x$–$C_y$ alkyl, wherein x is 1 and y is 3, includes $C_1$–$C_3$ alkyl radicals such as methyl, ethyl, propyl, and isopropyl. Examples of $C_1$–$C_6$ alkyl radicals include methyl, ethyl, propyl, isopropyl, n-butyl, tert-butyl, neopentyl, and n-hexyl. Examples of $C_1$–$C_{12}$ alkyl radicals include all the foregoing examples, as well as n-heptyl, n-octyl, n-nonyl, n-decyl, n-undecyl, and n-docecyl.

The term "$C_3$–$C_{12}$ alkenyl" as used herein refers to a straight- or branched-chain monovalent group derived from a hydrocarbon comprising three to twelve carbon atoms, respectively, which contain one or more carbon-carbon double bonds. Examples of $C_3$–$C_{12}$ alkenyl compounds include, but are not limited to, 1-propenyl, 1-methyl-2-butene-1-yl, 2-propenyl (allyl), and the like.

The term "$C_3$–$C_{12}$ alkynyl" used herein refers to a straight- or branched-chain monovalent group derived from a hydrocarbon comprising three to twelve carbon atoms, respectively, which contain one or more carbon-carbon triple bonds. Examples of $C_3$–$C_{12}$ alkynyl compounds are 1-propynyl, 2-propynyl (propargyl), and the like.

The term "aryl" as used herein refers to a mono-, fused bicyclic or fused tricyclic carbocyclic ring system having one or more aromatic rings including, but not limited to, phenyl, naphthyl, indanyl, indenyl, tetrahydronaphthyl, anthracenyl, phenanthrenyl, biphenylenyl, fluorenyl, and the like.

The term "substituted aryl" as used herein refers to an aryl group as defined above substituted by independent replacement of one, two or three of the hydrogen atoms thereon with Cl, Br, F, I, OH, CN, $C_1$–$C_3$ alkyl, $C_1$–$C_6$ alkoxy, $C_1$–$C_6$ alkoxy substituted with aryl, haloalkyl, thioalkoxy, amino, alkylamino, dialkylamino, mercapto, nitro, carboxaldehyde, carboxy, alkoxycarbonyl and carboxamide. Any one substitutent can also be an aryl, heteroaryl, or heterocycloalkyl group. Substituents can also include alkenyloxy, for example, methylenedioxy and ethylenedioxy. In addition, substituted aryl groups can also include tetrafluorophenyl and pentafluorophenyl.

The term "optionally substituted aryl" as used herein refers to an aryl group as defined above optionally substituted with a substituent as described for "substituted aryl".

The terms "halo", "halide", and "halogen" as used herein refer to an atom selected from fluorine, chlorine, bromine, and iodine.

The term "heteroaryl" as used herein refers to a cyclic aromatic radical having from five to ten ring atoms of which one ring atom is selected from S, O and N; one, two, or three ring atoms may be additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, tetrazolyl, thiophenyl, furanyl, quinolinyl, isoquinolinyl, and the like.

The term "heterocyclic", "heterocycle", and "heterocycloalkyl" as used herein refers to a non-aromatic partially unsaturated or fully saturated 3- to 10-membered ring system which includes single rings of 3 to 8 atoms in size and bi- or tricyclic ring systems which may include aromatic six-membered aryl or heteroaryl rings fused to a non-aromatic ring. These heterocyclic rings include those having from one to three heteroatoms independently selected from oxygen, sulfur and nitrogen, in which the nitrogen and sulfur heteroatoms may optionally be oxidized and the nitrogen heteroatom may optionally be quaternized.

Representative heterocycles include pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "substituted heteroaryl" as used herein refers to a heteroaryl group as defined above substituted by independent replacement of one, two or three of the hydrogen atoms thereon with Cl, Br, F, I, OH, cyano, $C_1$–$C_3$ alkyl, $C_1$–$C_6$ alkoxy, $C_1$–$C_6$ alkoxy substituted with aryl, haloalkyl, thioalkoxy, alkoxy, alkoxyalkoxy, amino, alkylamino, dialkylamino, mercapto, —SO$_3$H, nitro, carboxaldehyde, carboxy, alkoxycarbonyl and carboxamide. In addition, any one substitutent may be an aryl, arylalkyl, cycloalkyl, heteroaryl, or heterocycloalkyl group.

The term "optionally substituted heteroaryl" as used herein refers to a heteroaryl group as defined above optionally substituted with a substituent as described for "substituted heteroaryl".

The term "substituted heterocycloalkyl" as used herein, refers to a heterocycloalkyl group, as defined above, substituted by independent replacement of one, two or three of the hydrogen atoms thereon with Cl, Br, F, I, OH, cyano, $C_1$–$C_3$ alkyl, $C_1$–$C_6$ alkoxy, $C_1$–$C_6$ alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substitutent may be an aryl, heteroaryl, or heterocycloalkyl group.

The term "optionally substituted heterocycloalkyl" as used herein refers to a heterocycloalkyl group as defined above optionally substituted with a substituent as described for "substituted heterocycloalkyl".

The term "hydroxy-protecting group" as used herein refers to an easily removable group to which are known in the art to protect a hydroxyl group against undesirable reaction during synthetic procedures and to be selectively removable. The use of hydroxy-protecting groups is well-known in the art for protecting groups against undesirable reactions during a synthetic procedure and many such protecting groups are known, cf, for example T. H. Wiley & Sons, New York (1991). Examples of hydroxy-protecting groups are methylthiomethyl, tert-dimethylsilyl, tert-butyldiphenylsilyl, acyl substituted with an aromatic group, and the like.

The term "protected hydroxy" as used herein refers to a hydroxy group protected with a hydroxy protecting group as defined above including, but not limited to, benzoyl, acetyl, trimethylsilyl, triethylsilyl, methoxymethyl, and the like.

Examples of compounds which can be administered in the claimed method include, but are not limited to:

compound of formula III: $R^1$ is —$CH_2CH=CH(3$-quinolyl) and $R^2$ is —$CH_2CH_3$;

compound of formula III: $R^1$ is —$CH_2CH=CH(3$-quinolyl) and $R^2$ is —$CH_3$;

compound of formula III: $R^1$ is —$CH_2CH=CH(3$-quinolyl) and $R^2$ is —$CH_2CH(CH_3)_2$;

compound of formula III: $R^1$ is —$CH_2CH=CH(3$-quinolyl) and $R^2$ is —$CH_2$-phenyl;

compound of formula III: $R^1$ is —$CH_2CH=CH(3$-quinolyl) and $R^2$ is —$CH_2(4$-nitrophenyl);

compound of formula I: $R^1$ is —$CH_3$, $R^2$ is —$CH_2CH(CH_3)_2$ and $R^3$ is —OH;

compound of formula III: $R^1$ is —$CH_3$ and $R^2$ is —$CH_2$-phenyl;

compound of formula I: $R^1$ is —$CH_2(3$-iodophenyl), $R^2$ is —H and $R^3$ is —OH;

compound of formula III: $R^1$ is —$CH_2CH=CH(3$-quinolyl) and $R^2$ is —$CH_2CH_2CH_3$;

compound of formula III: $R^1$ is —$CH_2CH=CH(3$-quinolyl) and $R^2$ is —$CH_2CH_2CH_2CH_3$;

compound of formula III: $R^1$ is —$CH_2CH=CH_2$ and $R^2$ is —H;

compound of formula III: $R^1$ is —$CH_2CH=CH(3$-quinolyl) and $R^2$ is —$CH_2CO$(piperizine-N-phenyl); and compound of formula I: $R^1$ is —$CH_2(4$-phenylphenyl) and $R^2$ is —H and $R^3$ is —OH.

The compounds applied or administered in the method of the invention can have numerous asymmetric centers. Salt and ester derivatives of the compounds can be used for inhibiting the bacterial activity in the method. Except where otherwise noted, the invention contemplates the various stereoisomers and mixtures of the compounds, salts and ester derivatives.

An effective amount of the compound can inhibit the activity of macrolide or methicillin-resistant bacterial organism. An "effective" amount of the compound is any amount sufficient for inhibiting the activity of the bacterial strain, including the growth and reproductive activity of the organism. The compound can be administered in vitro, for example in an analytical assay or as part of a screening method, or in vivo, such as in a clinical setting for treatment of a bacterial infection.

Method for Treating a Bacterial Infection

In a second aspect, the invention relates to a method for treating a bacterial infection caused by a methicillin-resistant strain of staphylococci, comprising administering a therapeutically effective amount of a compound having a formula I, II or III to a patient in need.

The compounds can be administered as a pharmaceutically acceptable salt, ester, solvate or prodrug thereof. The method is useful, in particular, for treating an infection caused by MRSA.

The term "pharmaceutically acceptable salt" as used herein refers to those carboxylate salts, esters, and prodrugs of the compound of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. Pharmaceutically acceptable salts are well-known in the art and refer to the relatively non-toxic, inorganic and organic acid addition salts of the compound of the present invention. For example, S. M. Berge, et al. describe pharmaceutically acceptable salts in detail in *J. Pharmaceutical Sciences*, 66: 1–19 (1977) which is incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyrates, acrylates and ethylsuccinates.

The term "pharmaceutically acceptable solvate" represents an aggregate that comprises one or more molecules of the solute, such as a compound of the invention, with one or more molecules of solvent.

The term "pharmaceutically acceptable prodrug" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, 1987, both of which are incorporated herein by reference.

Any manner of delivering a therapeutically effective amount of the compound is suitable for the invention. The described compounds can be administered to a human or animal in a wide variety of dosage forms. Typically, the compound is administered as a pharmaceutical composition comprising the desired amount of the compound formulated together with one or more pharmaceutically acceptable carriers. The composition can be administered, for example, orally, parenterally, intraperitoneally, intracisternally, rectally, intravaginally, topically, or bucally.

The pharmaceutically acceptable carrier can be a non-toxic, inert solid, semi-solid or liquid filler, diluent, encapsulating material or formulation auxiliary. Examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate; and coloring agents, releasing agents, coating agents, sweetening, flavoring and perfuming agents. Preservatives and antioxidants are also suitable for the composition, according to the judgment of the formulator.

Orally administered dosage forms can include both liquid and solid dosage forms. Suitable liquid dosage forms include, for example, pharmaceutically acceptable emulsions, microemulsions, solutions, suspensions, syrups and elixirs. The liquid dosage forms can contain the active compound in combination with inert diluents, for example, water and/or other solvents or solubilizing agents, and emulsifiers. Examples of emulsifiers include, but are not limited to, ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. The oral compositions can also include adjuvants such as wetting agents, suspending agents, sweeteners, flavoring, and perfuming agents.

In a solid dosage form, the active compound is mixed with at least one inert, pharmaceutically acceptable excipient or carrier. Examples of solid dosage forms can include capsules, dragees, tablets, pills, powders, and granules. The pharmaceutically acceptable excipient or carrier comprises sodium citrate or dicalcium phosphate and/or fillers or extenders such as starches, lactose, sucrose, glucose, mannitol, and silicic acid; binders such as carboxymethylcellulose, alginates, gelatin, polyvinylpyrrolidinone, sucrose, and acacia; humectants such as glycerol; disintegrating agents such as agar-agar, calcium carbonate, potato or tapioca starch, alginic acid, certain silicates, and sodium carbonate; solution retarding agents such as paraffin; absorption accelerators such as quaternary ammonium compounds; wetting agents such as, for example, cetyl alcohol and glycerol monostearate; absorbents such as kaolin and bentonite clay, and lubricants such as talc, calcium stearate, magnesium stearate, solid polyethylene glycols, sodium lauryl sulfate, and mixtures thereof. The capsules, tablets and pills can also comprise buffering agents such as sodium and phosphate buffers.

To obtain a tablet, dragee, pill or capsule, the active compound is admixed with at least one inert diluent such as sucrose, lactose or starch, optionally in combination with tableting lubricants or other tableting aids such a magnesium stearate and microcrystalline cellulose. Tablets, dragees, capsules, pills, and granules can be prepared with coatings and shells for example enteric coatings, release controlling coatings and other pharmaceutically acceptable coatings. Opacifying agents can be incorporated in the dosage form to preferentially or exclusively release the compound in a designated portion of the intestinal tract, preferably in a delayed release formulation. Embedding compositions, including polymeric substances and waxes, are also suitable excipients for the solid dosage forms. The active compounds can also be in micro-encapsulated form with one or more excipients selected from materials previously described for the pharmaceutically acceptable carrier.

Parenterally administered injectable preparations, for example, sterile injectable aqueous or oleaginous suspensions can be formulated using suitable dispersing or wetting agents and suspending agents. The sterile injectable preparation can be a solution, suspension or emulsion in a nontoxic parenterally acceptable diluent or solvent, for example, as a solution in 1,3-butanediol. Pharmaceutically acceptable vehicles and solvents that are suitable for the injectable preparation include, for example, water, Ringer's solution, U.S.P. and isotonic sodium chloride solution. Sterile, fixed oils are conventionally employed as a solvent or suspending medium. Any bland fixed oil can be employed in the injectable preparation, including synthetic mono- or diglycerides. In addition, fatty acids such as oleic acid can be used in the preparation of injectable formulations.

To enjoy the full effect of the active compound, it is often desirable to slow the absorption of the drug from subcutaneous or intramuscular injection. The rate at which the drug is absorbed can be modified by combining the liquid suspension with a crystalline or amorphous material having poor water solubility, considering the crystal size and crystalline form of the material.

The rate of release of the active compound can be controlled by dissolving or preparing the active compound in an oil vehicle, for example as an injectable depot form. Injectable depot forms are made by forming microencapsule matrices of the drug in biodegradable polymers such as polylactide-polyglycolide. The depot forms are obtained by entrapping the active compound in liposomes or microemulsions, which are compatible with body tissues. The rate of release of the active agent can be modified depending upon the ratio of drug to polymer and the nature of the particular polymer employed. Examples of biodegradable polymers suitable for the injectable depot forms are poly(orthoesters), poly(anhydrides) and the like.

The injectable formulations can be sterilized by any method, for example, by filtration through a bacterial-retaining filter or by incorporating sterilizing agents in the form of sterile solid compositions, which can be dissolved or dispersed in sterile water or other sterile injectable medium prior to use.

Compositions for rectal or vaginal administration are preferably suppositories, which can be prepared by mixing the compounds of this invention with suitable non-irritating excipients or carriers such as cocoa butter, polyethylene glycol or a suppository wax. Suitable excipients are solid at ambient temperature and liquid at body temperature and therefore melt in the rectum or vaginal cavity and release the active compound.

The active compound can be administered topically or transdermally in the form of an ointment, paste, cream, lotion, gel, powder, solution, spray, inhalant or patch. The active component is admixed under sterile conditions with a pharmaceutically acceptable carrier and optionally with a preservative or buffer. The invention contemplates administering the active compound in the ear or eyes, for example as ear drops, eye drops or as an ocular patch.

The ointments, pastes, creams and gels can contain additional excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain the active compound in combination with additional excipients such as lactose, talc, silicic acid, aluminum hydroxide, calcium silicates and polyamide powder, or mixtures of these substances. The sprays typically contain a pharmaceutical propellant, for example, chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The administeration of a therapeutically effective amount of the active compound treats or prevents a bacterial infection in a patient in need. The active compound can be administered to a mammal, including either a human or an animal, in such amounts and for such time as is necessary to achieve the desired result. The prescribed therapeutically effective amount of the active compound refers a sufficient amount of the compound to treat bacterial infections, at a reasonable benefit/risk ratio applicable to any medical treatment. In practice, the total daily usage of the compounds and compositions of the present invention can be decided by the attending physician within the scope of sound medical judgment. It is well-within the purview of a competent attending physician to consider the disorder being treated; the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and other medically relevant factors in determining the therapeutic dose of the patient.

For the purpose of illustrating the invention and to provide guidance in the practice of the invention, the total daily dose of the active compounds administered to a human or other mammal can be, for example, from about 0.1 to 50 mg/kg body weight, or more preferably from about 1 to 25 mg/kg body weight. The total daily dose can be administered in single dose or in divided doses. The single dose compositions can contain such amounts or submultiples thereof to make up the daily dose. In general, treatment regimens according to the present invention comprise administration to a patient in need of such treatment from about 10 mg to about 2000 mg of a compound of the invention per day in a single or multiple doses.

Preparation of Compounds

Compounds of formula I, II or III can be prepared from erythromycin or a derivative thereof. Desired compounds of formula I, II and III can be accomplished by alkylation of the 6-O-position of an erythromycin A or ketolide substrate and conversion of the C-9 carbonyl group of the erythromycin A or ketolide substrate into a C-9 oxime.

Processes for preparing suitable starting compounds have been disclosed in U.S. Pat. Nos. 4,990,602 and 5,866,549, the disclosures of which are herein incorporated by reference. Commonly-owned U.S. patent application Ser. No. 08/646,477, filed on May 7, 1996, describes 6-O-substituted erythromycin and ketolide compounds and a process for preparing the same. Useful methods for alkylating the 6-O-position of erythromycin compounds have also been described in commonly-owned U.S. patent application Ser. No. 60/140,968, filed on Jun. 24, 1999, discussing palladium-catalyzed methods of alkylation.

Suitable substrates for preparing the described 6-O-substituted-9-oxime erythromycin and ketolide derivatives are compounds having a formula:

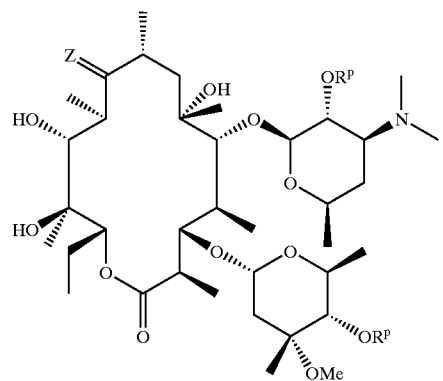

IV

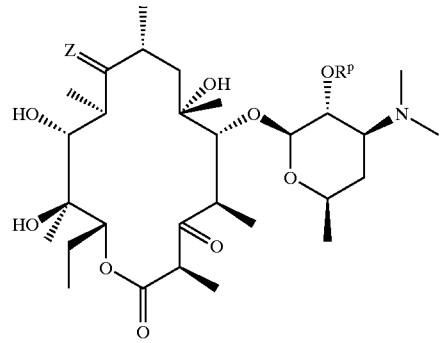

VI wherein Z is a C-9 carbonyl, an oxime, or a protected oxime and $R^P$ at each occurrence is independently selected from hydrogen or a hydroxy-protecting group. The substrate of formula IV can be prepared from a commercially available erythromycin A compound (available from Abbott Laboratories, Abbott Park, Ill., U.S.A.) using well-known conditions for protecting and deprotecting the 2'- and 4"-hydroxyl groups as well as converting the C-9 carbonyl into an oxime or protected oxime.

A compound having a formula V

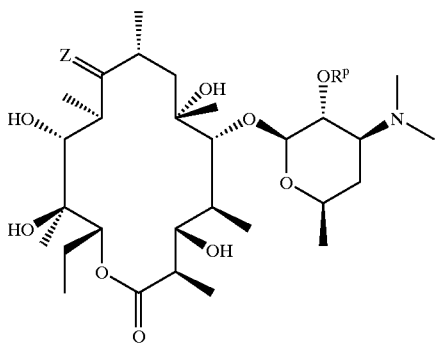

wherein Z and $R^p$ are as previously defined, can be obtained from the erythromycin compound of formula IV by removing the cladinose sugar under conditions for mild aqueous acid hydrolysis. Representative acids include dilute hydrochloric acid, sulfuric acid, perchloric acid, chloroacetic acid, dichloroacetic acid or trifluoroacetic acid. Suitable solvents for the reaction include methanol, ethanol, isopropanol, butanol and the like. Reaction times are typically 0.5 to 24 hours. The reaction temperature is preferably −10° C. to 70° C.

The 3-hydroxyl group of compound V can be oxidized under modified Swern oxidation procedure or Corey-Kim oxidation conditions to provide a compound of formula VI. Suitable oxidizing agents are N-chlorosuccinimide-dimethyl sulfide or carbodiimide-dimethylsulfoxide. In one example, the erythromycin compound of formula V is added into a pre-formed N-chlorosuccinimide and dimethyl sulfide complex in a chlorinated solvent, such as methylene chloride, at −10 to 25° C. After stirring for 0.5–4 hours, a tertiary amine, such as triethylamine or Hunig's base, is added to produce the corresponding ketone.

To obtain compounds of formula IV or VI, the C-9-carbonyl group of the erythromycin A can be protected as an oxime as represented by Z, wherein Z is N—O—$(CH_2)_s$—$R^x$, N—O—C(O)—$(CH_2)_s$—$R^x$, or N—O—C($R^y$)($R^z$)—O—$R^x$, wherein s is 0 to 5 and $R^x$ is (a) hydrogen, (b) alkyl, (c) substituted alkyl, (d) aryl, (e) substituted aryl, (f) heteroaryl, and (g) substituted heteroaryl, and wherein $R^y$ and $R^z$ are independently selected from (a) hydrogen, (b) unsubstituted $C_1$–$C_{12}$-alkyl, (c) $C_1$–$C_{12}$-alkyl substituted with aryl, and (d) $C_1$–$C_{12}$-alkyl substituted with substituted aryl, or $R^y$ and $R^z$ taken together with the carbon to which they are attached form a $C_3$–$C_{12}$-cycloalkyl ring. A preferred protected oxime group Z is N—O—(1-isopropoxycyclohexyl) or N—O—C(O)-phenyl (i.e. N—O-benzoyl). A more thorough discussion regarding the starting materials, reagents, and conditions for the conversion of erythromycin A (available from Abbott Laboratories, Abbott Park, Ill.) is described in U.S. Pat. Nos. 4,990,602; 4,331,803; 4,680,368; and 4,670,549; and European Patent Application EP 260,938.

The 2'- and 4"-hydroxy groups of the C-9 protected erythromycin A can be treated with a suitable hydroxy protecting reagent in an aprotic solvent. Hydroxy protecting reagents include, for example, acetic anhydride, benzoic anhydride, benzyl chloroformate, hexamethyldisilazane, or a trialkylsilyl chloride in an aprotic solvent. Examples of aprotic solvents are dichloromethane, chloroform, tetrahydrofuran (THF), N-methyl pyrrolidinone, dimethylsulfoxide, diethylsulfoxide, N,N-dimethylformamide (DMF), N,N-dimethylacetamide, hexamethylphosphoric triamide, a mixture thereof or a mixture of one of these solvents with ether, tetrahydrofuran, 1,2-dimethoxyethane, acetonitrile, ethyl acetate, acetone and the like. Aprotic solvents do not adversely affect the reaction, and are preferably dichloromethane, chloroform, DMF, tetrahydrofuran, N-methyl pyrrolidinone or a mixture thereof. The protection of the 2'- and optionally the 4"-hydroxy groups of the C-9 protected erythromycin A may be accomplished sequentially or simultaneously. Preferred protecting groups include, but are not limited to, acetyl, trimethylsilyl, and benzoyl. A thorough discussion of protecting groups and the solvents in which they are most effective is provided by T. W. Greene and P. G. M. Wuts in *Protective Groups in Organic Synthesis*, 3rd ed., John Wiley & Son, Inc., 1991.

Alkylation of a compound having the formula IV or VI affords the corresponding 6-O-substituted intermediate of the formula:

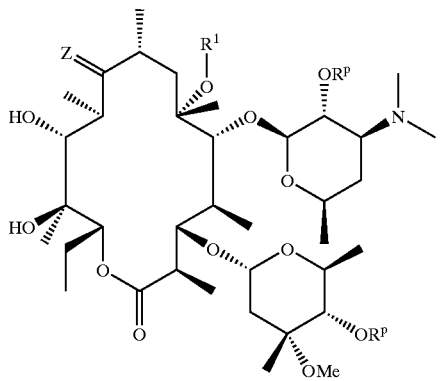

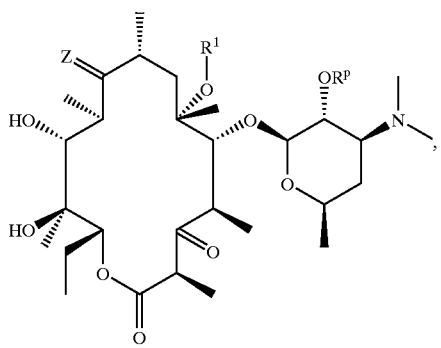

respectively, wherein Z, $R^1$ and $R^p$ are as previously defined. The alkylation of the 6-O-hydroxy group can be accomplished with an alkylating agent in the presence of base. Suitable alkylating agents include chloride, bromide, iodide or sulfonate derivatives of a desired alkyl, aryl, heteroaryl or heterocycloalkyl group, which is optionally substituted with one to three substituents defined for the group $R^1$. Specific examples of other alkylating agents are allyl bromide, propargyl bromide, benzyl bromide, 2-fluoroethyl bromide, 3-iodobenzyl bromide, 4-nitrobenzyl bromide, 4-chlorobenzyl bromide, 4-methoxybenzyl bromide, α-bromo-p-tolunitrile, cinnamyl bromide, methyl 4-bromocrotonate, crotyl bromide, 1-bromo-2-pentene, 3-bromo-1-propenyl phenyl sulfone, 3-bromo-1trimethylsilyl-1-propyne, 1-bromo-2-octyne, 1-bromo-2-butyne, 2-picolyl chloride, 3-picolyl chloride, 4-picolyl chloride, 4-phenylbenzyl chloride, 4-bromomethyl quinoline, bromoacetonitrile, epichlorohydrin, bromofluoromethane, bromonitromethane, methyl bromoacetate, methoxymethyl chloride, bromoacetamide, 2-bromoacetophenone, 1-bromo-2-butanone, bromochloromethane, bromomethyl phenyl sulfone, and 1,3-dibromo-1-propene. Examples of alkyl or aryl sulfonates are allyl tosylate, 3-phenylpropyl trifluoromethane sulfonate, and n-butylmethanesulfonate.

Examples of the solvents used are aprotic solvents such as dimethyl sulfoxide (DMSO), diethylsulfoxide, N,N-dimethylformamide, N,N-dimethylacetamide, N-methyl-2-pyrrolidone, hexamethylphosphoric triamide, mixtures thereof or mixtures of one of these solvents with ether, tetrahydrofuran, 1,2-dimethoxyethane, acetonitrile, ethyl acetate, or acetone. Examples of base which can be used are potassium hydroxide, cesium hydroxide, tetraalkylammonium hydroxide, sodium hydride, potassium hydride, and alkali metal alkoxides such as potassium isopropoxide, potassium tert-butoxide, and potassium iso-butoxide. An especially preferred method of carrying out the alkylation is treatment of the erythromycin or ketolide derivative with allyl bromide or propargyl bromide in a DMSO/THF mixture with potassium hydroxide or potassium t-butoxide as the base.

6-O-Allyl-substituted derivatives can be coupled with an aryl halide in the presence of Pd(II) or Pd(0) catalysts with promoters such as phosphines, arsines, amines, and inorganic bases in polar, aprotic solvents; see *Organic Reactions*, 1982, 27, 345–390. Preferably, the promoters are selected from triphenylphosphine, tri(o-tolyl)phosphine, triphenylarsine, pyridine and triethylamine, potassium carbonate, and cesium fluoride. The aprotic solvents are as previously defined such as dimethylformamide, dimethyl sulfoxide, dimethylethane, acetonitrile, tetrahydrofuran, or mixtures thereof. The reaction is accomplished at temperatures from about room temperature to about 150° C., depending on the reagents chosen and the nature of the aryl halide.

6-O-Propargyl groups can be further derivatized under Sonagashira conditions by combining the alkyne derivative with an aryl halide in the presence of a phosphine promoter and Cu(I) optionally in the presence of an organic base. Preferably, the organic base is triethylamine. Summary of the procedures, reagents, and solvents for coupling terminal alkynes with aryl halides is described in *Tetrahedron Lett.*, 1975, 50, 4467–4470.

The C9-oxime, wherein Z is a protected oxime, can be deprotected under neutral, acidic or basic conditions and deoximated to afford a compound of the formula:

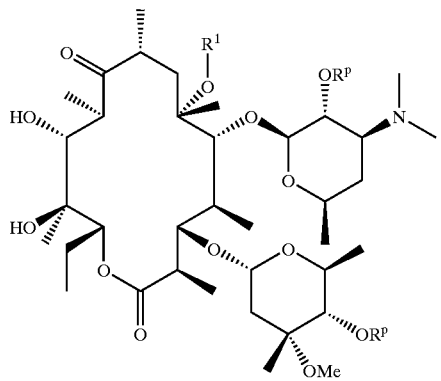

IX

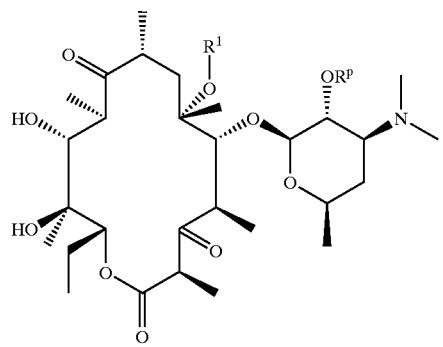

X respectively, wherein $R^1$ and $R^P$ are as previously defined. Exemplary conditions for deprotecting a protected oxime of the formula N—O—C(O)—(CH$_2$)$_s$—R$^x$ include, but are not limited to, treatment with an alcoholic solvent at room temperature or at reflux. Preferably, the C9-oxime is deprotected in this manner when $R^P$ is an ester, such as acetate or benzoate. Alcoholic solvents preferred for the deprotection are methanol or ethanol. Exemplary conditions for converting the protected oxime N—O—C(R$^y$)(R$^z$)—O—R$^x$, wherein $R^x$, $R^y$, and $R^z$ are as previously described, to the oxime (N—OH) involve treating the protected oxime with aqueous acid in acetonitrile. Aqueous acids suitable for the reaction include, but are not limited to, aqueous acetic acid, hydrochloric acid, and sulfuric acid. During the deprotection of the oxime, the 2'- and 4"-hydroxy protecting groups ($R^P$) can be removed in the process. A thorough discussion of the procedures, reagents and conditions for removing protecting groups is discussed by T. W. Greene and P. G. M. Wuts in *Protective Groups in Organic Synthesis*, 3rd ed., John Wiley & Son, Inc., (1991), which is herein incorporated by reference.

The deoximation reaction can be carried out by reacting the deprotected C9-oxime group with an inorganic sulfur oxide or an inorganic nitrite salt in a protic solvent to afford a C9-carbonyl group. Exemplary inorganic sulfur oxide compounds are sodium hydrogen sulfite, sodium thiosulfate, sodium sulfite, sodium metabisulfite, sodium dithionate, potassium thiosulfate, potassium metabisulfite, and the like. Suitable inorganic nitrite salts include, for example, sodium nitrite or potassium nitrite, and the like. Examples of the solvents used are protic solvents such as water, methanol, ethanol, propanol, isopropanol, trimethylsilanol, or a mixture of one or more of the mentioned solvents, and the like. The reaction is optionally carried out in the presence of an organic acid, such as formic acid, acetic acid and trifluoroacetic acid. Hydrochloric acid is also suitable for the reaction. The amount of acid used is from about 1 to about 10 equivalents of the amount of the deprotected C9-oxime compound. In a preferred embodiment, the C9-oxime group is deoximated using sodium nitrite and HCl in ethanol and water.

The 9-keto group of 6-hydroxyl or 6-O-substituted erythromycin or ketolide derivatives can be converted into a suitable oxime of the formula =N—O—R$^2$, wherein R$^2$ is as previously defined. The C9-oxime is prepared by the addition of hydroxylamine or a derivative thereof to the C9-ketone. From about 1 to about 3 molar equivalents of the hydroxylamine derivative are used for each mole of the starting erythromycin derivative.

The reaction can be carried out under acidic or basic conditions. Acidic conditions are preferred. The acidcatalyzed oximation reaction is accomplished in the presence of an inorganic or organic acid. The reaction is carried out in an alcoholic solvent. Suitable acids for the reaction include, but are not limited to, camphorsulfonic acid (CSA), acetic acid, formic acid, and the like. Examples of solvents suitable for the reaction are methanol, ethanol, isopropanol and the like.

To carry out the base-catalyzed oximation of the C9-carbonyl. A hydrochloride salt of hydroxylamine is introduced into a reaction mixture of the ketolide, sodium acetate and solvent. Preferably, from about 0.5 to about 10 molar equivalents of sodium acetate and hydroxylamine derivative are used for each mole of the starting ketolide material. The preferred solvent is ethanol.

Alternatively, treatment of the 9-keto group in a compound of formula IX or X with hydroxylamine affords the oxime wherein $R^2$ is hydrogen and the C9-oxime has the formula =N—O—H. The =N—O—H group can be reacted with the halide of a substituted- or unsubstituted alkyl, optionally substituted aryl, optionally substituted heteroaryl, or optionally substituted heterocycloalkyl group in the presence of base to obtain a group having a formula =N—O—$R^1$, wherein $R^1$ is as previously defined. The reaction is typically accomplished in an aprotic solvent, for example DMSO, diethylsulfoxide, N,N-dimethylformamide, N,N-dimethylacetamide, N-methyl-2-pyrrolidone, hexamethylphosphoric triamide, and mixtures thereof. The aprotic solvent can be suitably combined with ether, tetrahydrofuran, 1,2-dimethoxyethane, acetonitrile, ethyl acetate, or acetone. Suitable bases include, but are not limited to, potassium hydroxide, cesium hydroxide, tetraalkylammonium hydroxide, sodium hydride, potassium hydride, potassium isopropoxide, potassium tert-butoxide, and potassium iso-butoxide. The preferred reaction is accomplished with an alkyl or aryl bromide in N,N-dimethylformamide in the presence of potassium hydroxide.

Novel Compounds Having Activity Against MRSA

In a third aspect, the invention relates to a compound having a formula:

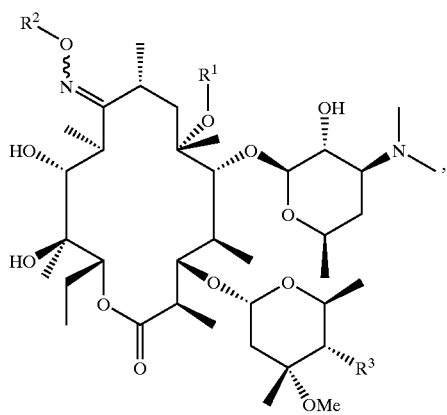

I

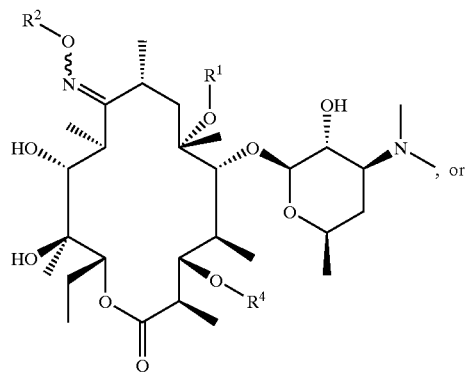

II

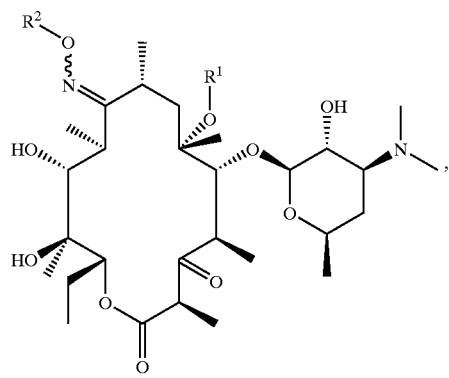

III or a pharmaceutically acceptable salt, ester, solvate or prodrug thereof, wherein:
$R^1$ is selected from the group consisting of:
  a hydrocarbon selected from the group consisting of $C_1$–$C_{12}$ alkyl, $C_3$–$C_{12}$ alkenyl, and $C_3$–$C_{12}$ alkynyl, wherein 1 to 3 carbons of said hydrocarbon is optionally replaced by an O, S or N heteroatom, or a group selected from —C(O)—, —C=N—, —C=N—O— and —N($R^5$)—; and wherein said hydrocarbon is optionally substituted with one to three substituents selected from —C(O)$R^6$, —S(O)$_n R^6$, —NHC(O)$R^6$, —NHC(O)NR$^7 R^8$, halogen, aryl, substituted aryl, heteroaryl, substituted heteroaryl and heterocycloalkyl, wherein n is 1 or 2;
$R^2$ is selected from the group consisting of:
  a. $C_1$–$C_{12}$ alkyl, wherein 1 to 3 carbons of the alkyl group is replaced with an O, S or N heteroatom, or a group selected from —C(O)—, —C=N—, —C=N—O— and —N($R^5$)—; or wherein the alkyl group is either independently or additionally substituted with one to three substituents selected from —C(O)$R^6$, —S(O)$_n R^6$, —NHC(O)$R^6$, —NHC(O)NR$^7 R^8$ and halogen;
  b. a hydrocarbon selected from $C_3$–$C_{12}$ alkenyl and $C_3$–$C_{12}$ alkynyl, wherein 1 to 3 carbons of said hydrocarbon is optionally replaced by an O, S or N heteroatom, or a group selected from —C(O)—, —C=N—, —C=N—O— and —N($R^5$)—; and wherein said hydrocarbon is optionally substituted with one to three substituents selected from —C(O)$R^6$, —S(O)$_n R^6$, —NHC(O)$R^6$, —NHC(O)NR$^7 R^8$, halogen, aryl, substituted aryl, heteroaryl, substituted heteroaryl and heterocycloalkyl; provided that when $R^1$ is $C_1$–$C_{12}$-alkyl in a compound of formula III, $R^2$ is not $C_3$–$C_{12}$-alkenyl, $C_3$–$C_{12}$-alkynyl, or $C_3$–$C_{12}$-alkenyl or $C_3$–$C_{12}$-alkynyl having 1 to 3 carbons replaced by a N heteroatom or a group selected from —N($R^5$)—;

c. optionally substituted aryl; and
d. optionally substituted heteroaryl;

$R^3$ is selected from the group consisting of
   a. —H,
   b. —OH,
   c. —OC(O)$R^9$,
   d. —OC(O)NH$R^9$, and
   e. —OC(O)O$R^9$;

$R^4$ is selected from the group consisting of
   a. —H,
   b. —C(O)$R^9$,
   c. —C(O)NH$R^9$, and
   d. —C(O)O$R^9$;

$R^5$ is hydrogen, $C_1$–$C_6$ alkyl, $C_1$–$C_6$ alkyl substituted with optionally substituted aryl or optionally substituted heteroaryl, optionally substituted aryl, or optionally substituted heteroaryl;

$R^6$ is hydrogen, alkyl optionally substituted with aryl or heteroaryl, optionally substituted aryl, or optionally substituted heteroaryl;

$R^7$ and $R^8$ are independently selected from the group consisting of hydrogen, $C_1$–$C_6$ alkyl, $C_1$–$C_6$ alkyl substituted with optionally substituted aryl or heteroaryl, optionally substituted aryl, or optionally substituted heteroaryl, or $R^7$ and $R^8$ taken together with the atoms to which they are attached form a $C_3$–$C_{12}$ cycloalkyl group; and $R^9$ is a hydrocarbon selected from the group consisting of $C_1$–$C_{12}$ alkyl, $C_3$–$C_{12}$ alkenyl, and $C_3$–$C_{12}$ alkynyl, wherein 1 to 3 carbons of said hydrocarbon is optionally replaced by an O, S or N heteroatom, or a group selected from —C(O)—, —C=N—, —C=N—O— and —N($R^5$)—; and wherein said hydrocarbon is optionally substituted with one to three substituents selected from —C(O)$R^6$, —S(O)$_n R^6$, —NHC(O)$R^6$, —NHC(O)N$R^7 R^8$, halogen, aryl, substituted aryl, heteroaryl, substituted heteroaryl and heterocycloalkyl.

The compounds can inhibit the bacterial activity of multi-drug resistant strains of bacteria, particularly MRSA. The claimed compounds are useful in the method of the invention for inhibiting activity against multi-drug resistant bacteria and for treating an infection caused by multi-drug resistant bacteria, such as MRSA.

The methods and compounds described above are intended to illustrate non-limiting examples of processes useful for preparing compounds administered in the method of the invention. The method of the invention and the compounds suitable for the invention can be better understood as described in the following Examples, which are meant as an illustration of the invention and are not intended to limit in any way the scope of the claimed invention as defined in the appended claims.

EXAMPLES

Example 1

Preparation of 6-O-[3-(3-quinolyl)-2-propen-1-yl]-3-descladinose-3-oxo-9-[(O-ethyl)oxime] Erythromycin A Compound of formula III, wherein $R^1$ is —CH$_2$CH=CH(3-quinolyl), $R^2$ is —CH$_2$CH$_3$ and $R^p$ is hydrogen Step (1): 6-O-[3-(3-Quinolyl)-2-propen-1-yl]-3-descladinose-3-oxo-2'-O-benzoyl Erythromycin A The title compound was prepared in accordance with the methods described in U.S. Pat. No. 5,866,549, which is herein incorporated by reference, and in particular by the procedure described for Example 18, Step 18a.

Step (2): 6-O-[3-(3-Quinolyl)-2-propen-1-yl]-3-descladinose-3-oxo-2'-O-benzoyl-9-[(O-ethyl)oxime] Erythromycin A To a stirred mixture of 6-O-[3-(3-quinolyl)-2-propen-1-yl]-3-descladinose-3-oxo-2'-O-benzoyl erythromycin A (0.84 g, 1.0 mmol) and O-ethylhydroxylamine hydrochloride (0.20 g, 2.0 mmol, 2.0 equiv) in ethanol (10 mL) was added camphor sulfonic acid (23 mg, 0.1 mmol, 0.1 equiv) at room temperature. The resulting mixture was degassed and warmed to 80° C. under nitrogen for 48 hours. After this time, the reaction was cooled to room temperature and concentrated to dryness. The remaining residue was dissolved in CH$_2$Cl$_2$ and washed with brine and water. The organic layer was dried (Na$_2$SO$_4$), filtered and concentrated to give the crude product. Purification via column chromatography (SiO$_2$, 50:50:2:0.1 hexane/ethyl acetate/methanol/ammonium hydroxide) gave 0.40 g (45%) of the desired product. The NMR and MS m/e 888 (M+H)$^+$ were consistent with the structure.

Step (3): 6-O-[3-(3-Quinolyl)-2-propen-1-yl]-3-descladinose-3-oxo-9-[(O-ethyl)oxime]Erythromycin A A solution of 6-O-[3-(3-quinolyl)-2-propen-1-yl]-3-descladinose-3-oxo-2'-O-benzoyl-9-[(O-ethyl)oxime] erythromycin A (0.40 g, 0.45 mmol) in methanol (20 mL) was stirred at room temperature for 1–6 days. After this time, the reaction mixture was concentrated and purified via column chromatography (SiO$_2$, 100:5:0.1 CH$_2$Cl$_2$/MeOH/NH$_4$OH) to provide 0.30 g (85%) of the title compound. The NMR and MS m/e 784 (M+H)$^+$ were consistent with the structure.

Examples 2–9

The following compounds were prepared according to the methods of Example 1, but substituting the amount (in molar equivalents) of the reagents named below for O-ethylhydroxylamine to obtain a compound of formula III wherein $R^2$ is the functional group defined in Table 1.

TABLE 1

| Example # | Reagent | Amount (equiv) | $R^2$ | MS (M + H)$^+$ m/e |
|---|---|---|---|---|
| 2 | CH$_3$ONH$_2$·HCl | 3 | (structure) | 770 |
| 3 | (isobutyl-ONH$_2$ structure) | 2 | (structure) | 812 |

TABLE 1-continued

| Example # | Reagent | Amount (equiv) | R² | MS (M + H)⁺ m/e |
|---|---|---|---|---|
| 4 | benzyl-ONH₂ | 2 | benzyl- | 846 |
| 5 | 4-nitrobenzyl-ONH₂ | 2 | 4-nitrobenzyl- | 891 |
| 6 | propyl-ONH₂ | 3 | propyl- | 798 |
| 7 | butyl-ONH₂ | 3 | butyl- | 812 |
| 8 | NH₂OH.HCl | 3 | —H | 786 |
| 9 | phenylpiperazinyl-C(O)CH₂-ONH₂ | 3 | phenylpiperazinyl-C(O)CH₂- | 958 |

Example 10

6-O-Methyl-9-[(O-isobutyl)oxime] Erythromycin A

Compound of formula I, wherein $R^1$ is —CH$_3$, $R^2$ is isobutyl, and $R^3$ is hydroxy Step (1): 6-O-Methyl Erythromycin A The title compound was prepared in accordance with the methods described in U.S. Pat. No. 4,331,803, which is herein incorporated by reference, and in particular by the procedure described for Example 1.

Step (2): 6-O-Methyl-9-oxime Erythromycin A

To a stirred suspension of the 6-O-methyl erythromycin A (10.0 g, 13.4 mmol) in isopropyl alcohol was added 50% hydroxylamine (aq.) (8.8 g, 0.134 mol, 10.0 equiv), followed by acetic acid (3.5 g). The reaction mixture was stirred at ambient temperature over night after which time it was warmed to 50° C. After three days, the reaction appeared complete by TLC (SiO$_2$, 0.5:10.0:89.5 NH$_4$OH/MeOH/CH$_2$Cl$_2$). The reaction was allowed to cool to room temperature at which time it was diluted with isopropyl acetate. The mixture was made basic (to litmus) using 4 N NaOH thus precipitating a white solid. This solid was collected via filtration to yield 8 g of the crude product. Purification by flash column chromatography using a gradient system (SiO$_2$, 100% CH$_2$Cl$_2$ then increasing to 0.5:10.0:89.5 NH$_4$OH/MeOH/CH$_2$Cl$_2$) gave the desired product. MS(ESI) m/e 763 (M+H)⁺.

Step (3): 6-O-Methyl-9-[(O-isobutyl)oxime] Erythromycin A

To a stirred solution of 6-O-methyl-9-oxime erythromycin A (0.25 g, 0.3 mmol) in DMF (10 mL) was added KOH (28 mg, 0.5 mmol, 1.5 equiv) followed by isobutyl bromide (43 μL, 0.4 mmol, 1.2 equiv) at room temperature under nitrogen. After six hours the reaction was poured into ice water and extracted with ethyl acetate (3×). The combined organic layers were dried over MgSO$_4$. Filtration and concentration (by rotary evaporation) gave the crude product. Purification via column chromatography (SiO$_2$, 0.5:10.0:89.5 NH$_4$OH/MeOH/CH$_2$Cl$_2$) gave the title compound. The NMR(CDCl$_3$) and MS(ESI) m/e 819 (M+H)⁺ were consistent with the structure. Elemental Analysis: Calculated for C$_{42}$H$_{78}$N$_2$O$_{13}$; Calculated: C: 61.59 H: 9.60 N: 3.42; Found: C: 61.57 H: 9.58 N: 3.34.

Example 11

6-O-Methyl-3-descladinose-3-oxo-9-[(O-benzyl)oxime] Erythromycin A

Compound of formula III, wherein $R^1$ is —CH$_3$ and $R^2$ —CH$_2$-phenyl

Step (1): 6-O-Methyl-3-descladinose-3-oxo-2'-O-benzol Erythromycin A

The title compound was prepared in accordance with the methods described in U.S. Pat. No. 5,866,549, which is herein incorporated by reference, and in particular by the procedure described for Example 1, Steps (e)–(g).

Step (2): 6-O-Methyl-3-descladinose-3-oxo Erythromycin A

A solution of 6-methyl-3-descladinose-3-oxo-2'-O-benzoyl erythromycin A (3.0 g, 4.3 mmol) in methanol (40 mL) was warmed to reflux for 16 hours. After cooling to room temperature, the reaction mixture was concentrated (by rotary evaporation) to give the crude product. Purification via column chromatography using a gradient system (SiO$_2$, 100% CH$_2$Cl$_2$ then increasing to 0.5:5.0:94.5 NH$_4$OH/MeOH/CH$_2$Cl$_2$) afforded 1.0 g (40%) of the desired product. MS(ESI) m/e 588 (M+H)$^+$.

Step (3): 6-O-Methyl-3-descladinose-3-oxo-9-oxime Erythromycin A

To a stirred solution of 6-O-methyl-3-descladinose-3-oxo erythromycin A (0.20 g, 0.3 mmol) in ethanol (5.0 mL) was added hydroxylamine hydrochloride (0.12 g, 1.7 mmol, 5.0 equiv) and sodium acetate (27 mg, 0.3 mmol, 1.0 equiv). The resulting solution was warmed to reflux for 24 hours, cooled to ambient temperature and concentrated (by rotary evaporation). The crude product was purified via column chromatography using a gradient system (SiO$_2$, 100% CH$_2$Cl$_2$ then increasing to 0.5:4.0:95.5 NH$_4$OH/MeOH/CH$_2$Cl$_2$) to give the desired product. MS(ESI) m/e 603 (M+H)$^+$.

Step (4): 6-O-Methyl-3-descladinose-3-oxo-9-[(O-benzyl)oxime] Erythromycin A

A stirred solution of 6-O-methyl-3-descladinose-3-oxo-9-oxime erythromycin A (0.46 g, 0.8 mmol) in DMF (15 mL) was cooled to 0° C. Potassium hydroxide (64 mg, 1.1 mmol, 1.5 equiv) was then introduced and the cooling bath was immediately removed. The benzyl bromide (0.11 mL, 0.9 mmol, 1.2 equiv) was subsequently added and the reaction was allowed to stir at ambient temperature overnight. After this time, the reaction was poured into water and ethyl acetate. The layers were separated and the aqueous phase was extracted with ethyl acetate (2×). The combined organic layers were dried (MgSO$_4$), filtered and concentrated (by rotary evaporation) to give the crude product. Purification via column chromatography using a gradient system (SiO$_2$, 100% CH$_2$Cl$_2$ then increasing to 0.5:3.0:96.5 NH$_4$OH/MeOH/CH$_2$Cl$_2$) gave the title compound. The NMR (CDCl$_3$) and MS(ESI) m/e 693 (M+H)$^+$ were consistent with the structure. Elemental analysis, Calculated for C$_{37}$H$_{60}$N$_2$O$_{10}$; Calculated: C: 64.14 H: 8.73 N: 4.04; Found: C: 63.87 H: 8.78 N: 3.88.

Example 12

Preparation of 6-O-[(3-Iodo)benzyl]-9-oxime Erythromycin A

Compound of formula I, wherein R$^1$ is —CH$_2$-(3-iodophenyl), R$^2$ is —H and R$^3$ is —OH Step (1): 2',4"-Bis-O-trimethylsilyl-9-[(O-isopropoxycyclohexyl)oxime]Erythromycin A The title compound was prepared in accordance with the methods described in U.S. Pat. No. 4,990,602, which is herein incorporated by reference, and in particular by the procedure described for Example 30, Step 2.

Step (2): 6-O-[(3-Iodo)benzyl]-2',4"-bis-O-trimethylsilyl-9-[(O-isopropoxycyclohexyl)oxime]Erythromycin A A solution of 2',4"-bis-O-trimethylsilyl-9-[(O-isopropoxycyclohexyl)oxime]erythromycin A (6.0 g, 5.8 mmol) and iodobenzyl bromide (4.3 g, 14.5 mmol, 2.5 equiv) in 1:1 THF/DMSO (40 mL) was cooled to 0° C. under nitrogen. Potassium t-butoxide (11.6 mL of a 1.0 M THF solution, 11.6 mmol, 2.0 equiv) was diluted with DMSO (10 mL) and added dropwise to the reaction mixture. Upon complete addition, the reaction was stirred overnight during which time it had warmed to ambient temperature. The reaction was quenched with water and extracted with ethyl acetate. The organic layer was washed with brine and dried (MgSO$_4$). Filtration and concentration (by rotary evaporation) gave the crude product which was flushed through a column of silica gel using 5% acetone/hexane. Concentration of the eluent gave 4.0 g of the product as a mixture which was used without further purification.

Step (3): 6-O-[(3-Iodo)benzyl]-9-oxime Erythromycin A

The crude 6-O-[(3-iodo)benzyl]-2',4"-bis-O-trimethylsilyl-9-[(O-isopropoxy-cyclohexyl)oxime] erythromycin A (4.0 g) was diluted with acetonitrile (10 mL), water (5 mL) and acetic acid (5 mL). The resulting mixture was stirred at room temperature for 2 days and concentrated (by rotary evaporation). The remaining residue was azeotroped with toluene to give the crude product. Purification via column chromatography using a gradient system (SiO$_2$, 100% CH$_2$Cl$_2$ then increasing to 0.5:10.0:89.5 NH$_4$OH/MeOH/CH$_2$Cl$_2$) gave the title compound. The NMR (CDCl$_3$) and MS(ESI) m/e 965 (M+H)$^+$ were consistent with the structure.

Example 13

Preparation of 6-O-[(4-Phenyl)benzyl]-9-oxime Erythromycin A

Compound of formula I, wherein R$^1$ is —CH$_2$-(4-phenylphenyl), R$^2$ is hydrogen and R$^3$ is hydroxy Step (1): 2',4"-Bis-O-trimethylsilyl-9-[(O-isopropoxycyclohexyl)oxime] Erthromycin A The title compound was prepared in accordance with the methods described in U.S. Pat. No. 4,990,602, which is herein incorporated by reference, and in particular by the procedure described for Example 30, Step 2.

Step (2): 6-O-[(4-Phenyl)benzyl]-2',4"-bis-O-trimethylsilyl-9-[(O-isopropoxycyclohexyl)-oxime]Erythromycin A The 2',4"-bis-O-trimethylsilyl-9-[(O-isopropoxycyclohexyl)oxime] erythromycin A (1.5 g, 1.5 mmol) and 4-phenyl-benzyl bromide (0.6 g, 3.0 mmol, 2.0 equiv) were combined in 1:1 THF/DMSO (8 mL) and cooled to 0° C. Potassium t-butoxide (3.0 mL of a 1.0 M THF solution, 3.0 mmol, 2.0 equiv) was diluted with DMSO (3 mL) and added dropwise into the reaction mixture. Upon complete addition, the reaction was stirred overnight during which time it had warmed to ambient temperature. The reaction was quenched with water and extracted with ethyl acetate (2×). The combined organic layers were dried (MgSO$_4$), filtered and concentrated (by rotary evaporation) to give the crude product which was used without further purification.

Step (3): 6-O-[(4-Phenyl)benzyl]-9-oxime Erythromycin A

The crude 6-O-[(4-phenyl)benzyl]-2',4"-bis-O-trimethylsilyl-9-[(O-isopropoxy-cyclohexyl)oxime] erythromycin A (2.0 g) was dissolved in acetonitrile (5.0 mL), water (2.5 mL) and acetic acid (2.5 mL) and stirred at ambient temperature overnight. After this time, the reaction mixture was concentrated (by rotary evaporation) and the remaining residue was azeotroped with toluene. Purification via flash column chromatography using a gradient system (SiO$_2$, 100% CH$_2$Cl$_2$ then increasing to 0.5:10.0:89.5 NH$_4$OH/MeOH/CH$_2$Cl$_2$) gave the title compound. The NMR(CDCl$_3$) and MS (ESI) m/e 915 (M+H)$^+$ were consistent with the structure.

Example 14

In Vitro Antibacterial Activity Against Resistant *Staphylococcus aureus* 1775

Representative compounds of the present invention were assayed in vitro for antibacterial activity as follows: Petri dishes containing successive aqueous dilutions of the test compound mixed with 10 mL of sterilized Brain Heart Infusion (BHI) agar (Difco 0418-01-5) were prepared. Each plate was inoculated with 1:100 dilutions of a different microorganism, using a Steers replicator block. The inoculated plates were incubated at 35–37° C. for 20 to 24 hours. In addition, a control plate, using BHI agar containing no test compound, was prepared and incubated at the beginning and end of each test.

An additional plate containing a compound having known susceptibility patterns for the organisms being tested and belonging to the same antibiotic class as the test compound was also prepared and incubated as a further control, as well as to provide test-to-test comparability. Erythromycin A was used for this purpose.

After incubation, each plate was visually inspected. The minimum inhibitory concentration (MIC) was defined as the lowest concentration of drug yielding no growth, a slight haze, or sparsely isolated colonies on the inoculum spot as compared to the growth control. The results of this assay, shown below in Table 2, demonstrate the antibacterial activity of the compounds of the invention.

TABLE 2

| Compound | MIC (µg/ml) | |
| --- | --- | --- |
| | S. aureus A-5278 | S. aureus 1775 |
| Erythromycin | >100 | >100 |
| Methicillin | >100 | >100 |
| Ex. 1 | 25 | 12.5 |
| Ex. 2 | 25 | 25 |
| Ex. 3 | 12.5 | 12.5 |
| Ex. 4 | 25 | 12.5 |
| Ex. 5 | >100 | 50 |
| Ex. 6 | 100 | 25 |
| Ex. 7 | 100 | 25 |
| Ex. 9 | 50 | 50 |
| Ex. 12 | 25 | 25 |
| Ex. 13 | 50 | 25 |

What is claimed is:

1. A method of inhibiting the activity of methicillin-resistant bacteria in a mammal, comprising administering to the mammal an effective amount of a compound of the formula

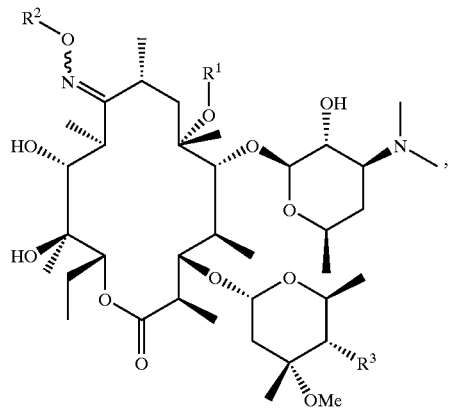

I a compound of the formula

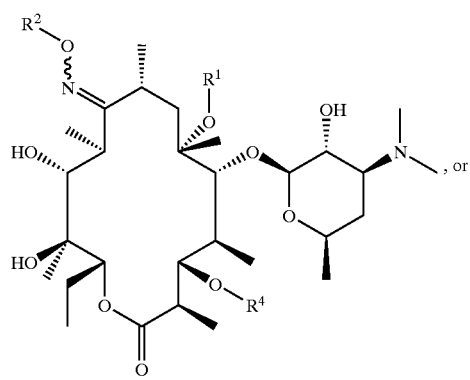

II a compound of the formula

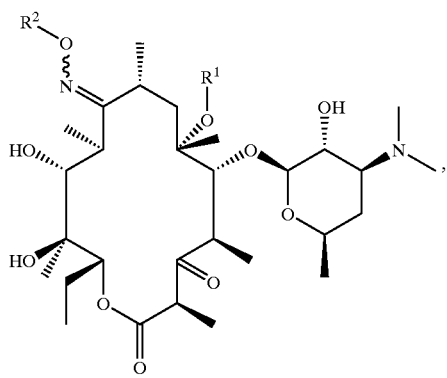

III wherein
R$^1$ is selected from the group consisting of
a hydrocarbon selected from the group consisting of C$_1$–C$_{12}$ alkyl, C$_3$–C$_{12}$ alkenyl, and C$_3$–C$_{12}$ alkynyl, wherein 1 to 3 carbons of said hydrocarbon are optionally replaced by an O, S or N heteroatom or a group selected from the group consisting of —C(O)—, —C=N—, —C=N—O— and —N(R$^5$)—; and wherein said hydrocarbon is optionally substituted with one to three substituents selected from the group consisting of —C(O)R$^6$, —S(O)$_n$R$^6$, —NHC(O)R$^6$, —NHC(O)NR$^7$R$^8$, halogen, aryl, substituted aryl, heteroaryl, substituted heteroaryl and heterocycloalkyl, wherein n is 1 or 2;
R$^2$ is selected from the group consisting of
(a) hydrogen,
(b) a hydrocarbon selected from the group consisting of C$_1$–C$_{12}$ alkyl, C$_3$–C$_{12}$ alkenyl, and C$_3$–C$_{12}$ alkynyl, wherein 1 to 3 carbons of said hydrocarbon are optionally replaced by an O, S or N heteroatom or a group selected from the group consisting of —C(O)—, —C=N—, —C=N—O— and —N(R$^5$)—; and wherein said hydrocarbon is optionally substituted with one to three substituents selected from the group consisting of —C(O)R$^6$, —S(O)$_n$R$^6$, —NHC(O)R$^6$, —NHC(O)NR$^7$R$^8$, halogen, aryl, substituted aryl, heteroaryl, substituted heteroaryl and heterocycloalkyl;
(c) optionally substituted aryl; and
(d) optionally substituted heteroaryl;

R³ is selected from the group consisting of
(a) —H,
(b) —OH,
(c) —OC(O)R⁹,
(d) —OC(O)NHR⁹, and
(e) —OC(O)OR⁹;

R⁴ selected from the group consisting of
(a) —H,
(b) —C(O)R⁹,
(c) —C(O)NHR⁹, and
(d) —C(O)OR⁹;

R⁵ is hydrogen, $C_1$–$C_6$ alkyl, $C_1$–$C_6$ alkyl substituted with optionally substituted aryl or optionally substituted heteroaryl, optionally substituted aryl, or optionally substituted heteroaryl;

R⁶ is hydrogen, alkyl optionally substituted with aryl or heteroaryl, optionally substituted aryl, or optionally substituted heteroaryl;

R⁷ and R₈ are independently selected from the group consisting of hydrogen, $C_1$–$C_6$ alkyl, $C_1$–$C_6$ alkyl substituted with optionally substituted aryl or heteroaryl, optionally substituted aryl, or optionally substituted heteroaryl, or R⁷ and R⁸ taken together with the atoms to which they are attached form a $C_3$–$C_{12}$ cycloalkyl group; and R⁹ is a hydrocarbon selected from the group consisting of $C_1$–$C_{12}$ alkyl, $C_3$–$C_{12}$ alkenyl, and $C_3$–$C_{12}$ alkynyl, wherein 1 to 3 carbons of said hydrocarbon are optionally replaced by an O, S or N heteroatom, or a group selected from the group consisting of —C(O)—, —C=N—, —C=N—O— and —N(R⁵)—; and wherein said hydrocarbon is optionally substituted with one to three substituents selected from the group consisting of —C(O)R⁶, —S(O)$_n$R⁶, —NHC(O)R⁶, —NHC(O)NR⁷R⁸, halogen, aryl, substituted aryl, heteroaryl, substituted heteroaryl and heterocycloalkyl.

2. The method according to claim 1, wherein R¹ is selected from the group consisting of —CH₃; —CH₂CH=CH; —CH₂(3-iodophenyl); —CH₂CH=CH (3-quinolyl); and —CH₂(4-phenylphenyl).

3. The method according to claim 1, wherein R² is selected from the group consisting of hydrogen; —CH₂-phenyl; —CH₂CH₃; —CH₂CH(CH₃)₂; —CH₃; —CH₂CH₂CH₂CH₃; —CH₂(4-nitrophenyl); and —CH₂CO (piperizine-N-phenyl).

4. The method according to claim 1, wherein the compound is selected from the group consisting of:
compound of formula III: R¹ is —CH₂CH=CH(3-quinolyl) and R² is —CH₂CH₃;
compound of formula III: R¹ is —CH₂CH=CH(3-quinolyl) and R² is —CH₃;
compound of formula III: R¹ is —CH₂CH=CH(3-quinolyl) and R² is —CH₂CH(CH₃)₂;
compound of formula III: R¹ is —CH₂CH=CH(3-quinolyl) and R² is —CH₂-phenyl;
compound of formula III: R¹ is —CH₂CH=CH(3-quinolyl) and R² is —CH₂(4-nitrophenyl),
compound of formula I: R¹ is —CH₃, R² is —CH₂CH (CH₃)₂ and R³ is —OH;
compound of formula III: R¹ is —CH₃ and R² is —CH₂-phenyl;
compound of formula I: R¹ is —CH₂(3-iodophenyl), R² is —H and R³ is —OH;
compound of formula III: R¹ is —CH₂CH=CH(3-quinolyl) and R² is —CH₂CH₂CH₃;
compound of formula III: R¹ is —CH₂CH=CH(3-quinolyl) and R² is —CH₂CH₂CH₂CH₃;
compound of formula III: R¹ is —CH₂CH=CH₂ and R² is —H;
compound of formula III: R¹ is —CH₂CH=CH(3-quinolyl) and R² is —CH₂CO(piperizine-N-pbenyl); and
compound of formula I: R¹ is —CH₂(4-phenylphenyl) and R² is —H and R³ is —OH.

5. The method according to claim 1, wherein the bacteria is a methicillin-resistant strain of *Staphylococcus aureus*.

6. A method of treating bacterial infection caused by a methicillin-resistant strain of bacteria, comprising administering to a patient in need a therapeutically effective amount of a compound of the formula

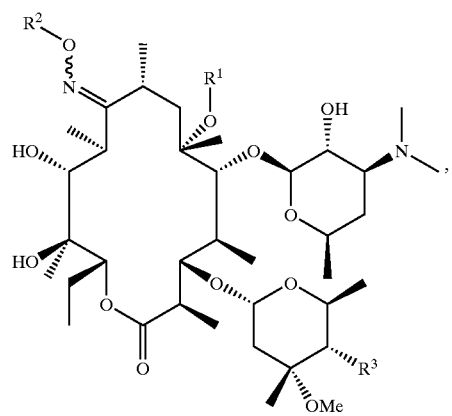

I a compound of the formula

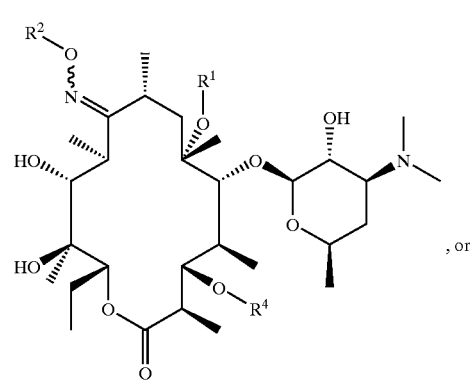

II

, or a compound of the formula

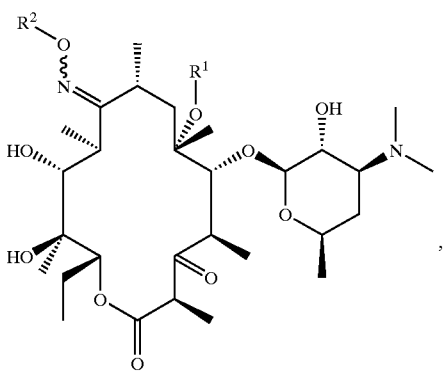

wherein
R$^1$ is selected from the group consisting of
a hydrocarbon selected from the group consisting of C$_1$–C$_{12}$ alkyl, C$_3$–C$_{12}$ alkenyl, and C$_3$–C$_{12}$ alkynyl, wherein 1 to 3 carbons of said hydrocarbon are optionally replaced by an O, S, or N heteroatom or a group selected from the group consisting of —C(O)—, —C=N—, —C=N—O— and —N(R$^5$)—; and wherein said hydrocarbon is optionally substituted with one to three substituents selected from —C(O)R$^6$, —S(O)$_n$R$^6$, —NHC(O)R$^6$, —NHC(O)NR$^7$R$^8$, halogen, aryl, substituted aryl, heteroaryl, substituted heteroaryl and heterocycloalkyl, wherein n is 1 or 2;
R$^2$ is selected from the group consisting of
(a) hydrogen,
(b) a hydrocarbon selected from the group consisting of C$_1$–C$_{12}$ alkyl, C$_3$–C$_{12}$ alkenyl, and C$_3$–C$_{12}$ alkynyl, wherein 1 to 3 carbons of said hydrocarbon are optionally replaced by an O, S or N heteroatom or a group selected from the group consisting of —C(O)—, —C=N—, —C=N—O— and —N(R$^5$)—; and wherein said hydrocarbon is optionally substituted with one to three substituents selected from the group consisting of —C(O)R$^6$, —S(O)$_n$R$^6$, —NHC(O)R$^6$, —NHC(O)NR$^7$R$^8$, halogen, aryl, substituted aryl, heteroaryl, substituted heteroaryl and heterocycloalkyl;
(c) optionally substituted aryl; and
(d) optionally substituted heteroaryl;
R$^3$ is selected from the group consisting of
(a) —H,
(b) —OH,
(c) —OC(O)R$^9$,
(d) —OC(O)NHR$^9$, and
(e) —OC(O)OR$^9$;
R$^4$ is selected from the group consisting of
(a) —H,
(b) —C(O)R$^9$,
(c) —C(O)NHR$^9$, and
(d) —C(O)OR$^9$;
R$^5$ is hydrogen, C$_1$–C$_6$ alkyl, C$_1$–C$_6$ alkyl substituted with optionally substituted aryl or optionally substituted heteroaryl, optionally substituted aryl, or optionally substituted heteroaryl;
R$^6$ is hydrogen, alkyl optionally substituted with aryl or heteroaryl, optionally substituted aryl, or optionally substituted heteroaryl;

R$^7$ and R$^8$ are independently selected from the group consisting of hydrogen, C$_1$–C$_6$ alkyl, C$_1$–C$_6$ alkyl substituted with optionally substituted aryl or heteroaryl, optionally substituted aryl, or optionally substituted heteroaryl, or R$^7$ and R$^8$ taken together with the atoms to which they are attached form a C$_3$–C$_{12}$ cycloalkyl group; and
R$^9$ is a hydrocarbon selected from the group consisting of C$_1$–C$_{12}$ alkyl, C$_3$–C$_{12}$ alkenyl, and C$_3$–C$_{12}$ alkynyl, wherein 1 to 3 carbons of said hydrocarbon are optionally replaced by an O, S or N heteroatom, or a group selected from the group consisting of —C(O)—, —C=N—, —C=N—O— and —N(R$^5$)—; and wherein said hydrocarbon is optionally substituted with one to three substituents selected from the group consisting of —C(O)R$^6$, —S(O)$_n$R$^6$, —NHC(O)R$^6$, —NHC(O)NR$^7$R$^8$, halogen, aryl, substituted aryl, heteroaryl, substituted heteroaryl and heterocycloalkyl.

7. The method according to claim 6, wherein the compound is selected from the group consisting of:
compound of formula III: R$^1$ is —CH$_2$CH=CH(3-quinolyl) and R$^2$ is —CH$_2$CH$_3$;
compound of formula III: R$^1$ is —CH$_2$CH=CH(3-quinolyl) and R$^2$ is —CH$_3$;
compound of formula III: R$^1$ is —CH$_2$CH=CH(3-quinolyl) and R$^2$ is —CH$_2$CH(CH$_3$)$_2$;
compound of formula III: R$^1$ is —CH$_2$CH=CH(3-quinolyl) and R$^2$ is —CH$_2$-phenyl;
compound of formula III: R$^1$ is —CH$_2$CH=CH(3-quinolyl) and R$^2$ is —CH$_2$(4-nitrophenyl);
compound of formula I: R$^1$ is —CH$_3$, R$^2$ is —CH$_2$CH(CH$_3$)$_2$ and R$^3$ is —OH;
compound of formula III: R$^1$ is —CH$_3$ and R$^2$ is —CH$_2$-phenyl;
compound of formula I: R$^1$ is —CH$_2$(3-iodophenyl), R$^2$ is —H and R$^3$ is —OH;
compound of formula III: R$^1$ is —CH$_2$CH=CH(3-quinolyl) and R$^2$ is —CH$_2$CH$_2$CH$_3$;
compound of formula III; R$^1$ is —CH$_2$CH=CH(3-quinolyl) and R$^2$ is —CH$_2$CH$_2$CH$_2$CH$_3$;
compound of formula III: R$^1$ is —CH$_2$CH=CH$_2$ and R$^2$ is —H;
compound of formula III: R$^1$ is —CH$_2$CH=CH(3-quinolyl) and R$^2$ is —CH$_2$CO(piperizine-N-phenyl); and
compound of formula I: R$^1$ is —CH$_2$(4-phenylphenyl) and R$^2$ is —H and R$^3$ is —OH.

8. The method according to claim 6, wherein the bacteria is *Staphylococcus aureus*.

9. The method according to claim 6, wherein said compound is administered orally, parenterally, intraperitoneally, intracisternally, rectally, intravaginally, topically or bucally.

10. The method according to claim 6, wherein said compound is administered as a capsule, dragee, elixir, emulsion, granule, microemulsion, tablet, pill, powder, solution, suspension, syrup, spray, suppository, or patch.

11. The method according to claim 6, wherein said compound is administered to a human or an animal.

12. The method according to claim 6, wherein said compound is administered in an amount from about 0.1 milligram per kilogram of body weight to about 50 milligrams per kilogram of body weight.

13. The method according to claim 12, wherein said compound is administered in an amount from about 1 milligram per kilogram of body weight to about 25 milligrams per kilogram of body weight.

14. The method according to claim 12, wherein said compound is administered in a single dose.

15. The method according to claim 12, wherein said compound is administered in a divided dose to obtain a total daily dose in an amount from about 0.1 milligram per kilogram of body weight to about 50 milligrams per kilogram of body weight.

16. The method according to claim 15, wherein said compound is administered in an amount from about 1 milligram per kilogram of body weight to about 25 milligrams per kilogram of body weight.

17. A compound having the formula

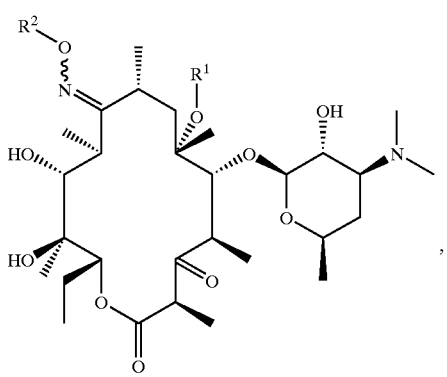

III or a pharmaceutically acceptable salt, ester, solvate or prodrug thereof, wherein $R^1$ is selected from the group consisting of
  a hydrocarbon selected from the group consisting of $C_1$–$C_{12}$ alkyl, $C_3$–$C_{12}$ alkenyl, and $C_3$–$C_{12}$ alkynyl, wherein 1 to 3 carbons of said hydrocarbon is optionally replaced by an O, S or N heteroatom, or a group selected from the group consisting of —C(O)—, —C=N—, —C=N—O— and —N($R^5$)—; and wherein said hydrocarbon is optionally substituted with one to three substituents selected from the group consisting of —C(O)$R^6$, —S(O)$_n R^6$, —NHC(O)$R^6$, —NHC(O)N$R^7 R^8$, halogen, aryl, substituted aryl, heteroaryl, substituted heteroaryl and heterocycloalkyl, wherein n is 1 or 2;

$R^2$ selected from the group consisting of
  (a) hydrogen,
  (b) a hydrocarbon selected from the group consisting of $C_1$–$C_{12}$ alkyl, $C_3$–$C_{12}$ alkenyl, and $C_3$–$C_{12}$ alkynyl, wherein 1 to 3 carbons of said hydrocarbon is optionally replaced by an O, S or N heteroatom, or a group selected from the group consisting of —C(O)—, —C=N—, —C=N—O— and —N($R^5$)—; and wherein said hydrocarbon is optionally substituted with one to three substituents selected from the group consisting of —C(O)$R^6$, —S(O)$_n R^6$, —NHC(O)$R^6$, —NHC(O)N$R^7 R^8$, halogen, aryl, substituted aryl, heteroaryl, substituted heteroaryl and heterocycloalkyl;
  (c) optionally substituted aryl; and
  (d) optionally substituted heteroaryl;

$R^3$ is selected from the group consisting of
  (a) —H,
  (b) —OH,
  (c) —OC(O)$R^9$,
  (d) —OC(O)NH$R^9$, and
  (e) —OC(O)O$R^9$;

$R^4$ is selected from the group consisting of
  (a) —H,
  (b) —C(O)$R^9$,
  (c) —C(O)NH$R^9$, and
  (d) —C(O)O$R^9$;

$R^5$ is hydrogen, $C_1$–$C_6$ alkyl, $C_1$–$C_6$ alkyl substituted with optionally substituted aryl or optionally substituted heteroaryl, optionally substituted aryl, or optionally substituted heteroaryl;

$R^6$ is hydrogen, alkyl optionally substituted with aryl or heteroaryl, optionally substituted aryl, or optionally substituted heteroaryl;

$R^7$ and $R^8$ are independently selected from the group consisting of hydrogen, $C_1$–$C_6$ alkyl, $C_1$–$C_6$ alkyl substituted with optionally substituted aryl or heteroaryl, optionally substituted aryl, or optionally substituted heteroaryl, or $R^7$ and $R^8$ taken together with the atoms to which they are attached form a $C_3$–$C_{12}$ cycloalkyl group; and $R^9$ is a hydrocarbon selected from the group consisting of $C_1$–$C_{12}$ alkyl, $C_3$–$C_{12}$ alkenyl, and $C_3$–$C_{12}$ alkynyl, wherein 1 to 3 carbons of said hydrocarbon are optionally replaced by an O, S or N heteroatom, or a group selected from the group consisting of —C(O)—, —C=N—, —C=N—O— and —N($R^5$)—; and wherein said hydrocarbon is optionally substituted with one to three substituents selected from the group consisting of —C(O)$R^6$, —S(O)$_n R^6$, —NHC(O)$R^6$, —NHC(O)N$R^7 R^8$, halogen, aryl, substituted aryl, heteroaryl, substituted heteroaryl and heterocycloalkyl.

18. A compound having the formula

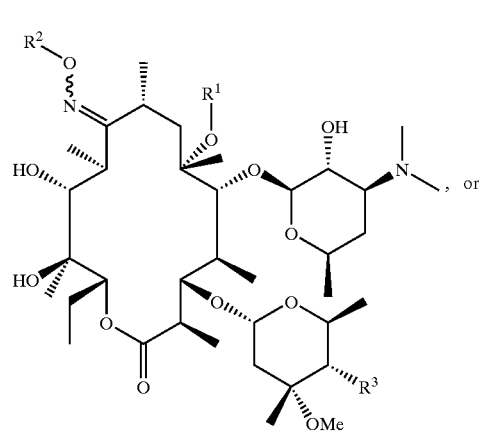

I

, or

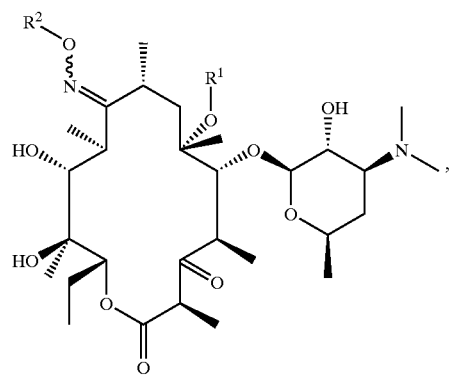

III wherein
$R^1$ is selected from the group consisting of a hydrocarbon selected from the group consisting of $C_3$–$C_{12}$ alkyl, $C_3$–$C_{12}$ alkenyl, and $C_3$–$C_{12}$ alkynyl, wherein 1 to 3 carbons of said $C_3$–$C_{12}$ alkenyl, and $C_3$–$C_{12}$ alkynyl are optionally replaced by an O, S or N heteroatom or a group selected from the group consisting of —C(O)—, —C=N—, —C=N—O— and —N($R^5$)—; and wherein said hydrocarbon is optionally substituted with one to three substituents selected from the group consisting of —C(O)$R^6$, —S(O)$_n R^6$, —NHC(O)$R^6$, —NHC(O)N$R^7 R^8$, halogen, aryl, substituted aryl, heteroaryl, substituted heteroaryl and heterocycloalkyl, wherein n is 1 or 2;

$R^2$ is selected from the group consisting of
 (a) hydrogen,
 (b) a hydrocarbon selected from the group consisting of $C_1$–$C_{12}$ alkyl, $C_3$–$C_{12}$ alkenyl, and $C_3$–$C_{12}$ alkynyl, wherein 1 to 3 carbons of said hydrocarbon are optionally replaced by an O, S or N heteroatom or a group selected from the group consisting of —C(O)—, —C=N—, —C=N—O— and —N($R^5$)—; and wherein said hydrocarbon is optionally substituted with one to three substituents selected from the group consisting of —C(O)$R^6$, —S(O)$_n R^6$, —NHC(O)$R^6$, —NHC(O)N$R^7 R^8$, halogen, aryl, substituted aryl, heteroaryl, substituted heteroaryl and heterocycloalkyl;
 (c) optionally substituted aryl; and
 (d) optionally substituted heteroaryl;

$R^3$ is selected from the group consisting of
 (a) —H,
 (b) —OH,
 (c) —OC(O)$R^9$,
 (d) —OC(O)NH$R^9$, and
 (e) —OC(O)O$R^9$;

$R^4$ is selected from the group consisting of
 (a) —H,
 (b) —C(O)$R^9$,
 (c) —C(O)NH$R^9$, and
 (d) —C(O)O$R^9$;

$R^5$ is hydrogen, $C_1$–$C_6$ alkyl, $C_1$–$C_6$ alkyl substituted with optionally substituted aryl or optionally substituted heteroaryl, optionally substituted aryl, or optionally substituted heteroaryl;

$R^6$ is hydrogen, alkyl optionally substituted with aryl or heteroaryl, optionally substituted aryl, or optionally substituted heteroaryl;

$R^7$ and $R^8$ are independently selected from the group consisting of hydrogen, $C_1$–$C_6$ alkyl, $C_1$–$C_6$ alkyl substituted with optionally substituted aryl or heteroaryl, optionally substituted aryl, or optionally substituted heteroaryl, or $R^7$ and $R^8$ taken together with the atoms to which they are attached form a $C_3$–$C_{12}$ cycloalkyl group; and $R^9$ is a hydrocarbon selected from the group consisting of $C_1$–$C_{12}$ alkyl, $C_3$–$C_{12}$ alkenyl, and $C_3$–$C_{12}$ alkynyl, wherein 1 to 3 carbons of said hydrocarbon are optionally replaced by an O, S or N heteroatom, or a group selected from the group consisting of —C(O)—, —C=N—, —C=N—O— and —N($R^5$)—; and wherein said hydrocarbon is optionally substituted with one to three substituents selected from the group consisting of —C(O)$R^6$, —S(O)$_n R^6$, —NHC(O)$R^6$, —NHC(O)N$R^7 R^8$, halogen, aryl, substituted aryl, heteroaryl, substituted heteroaryl and heterocycloalkyl.

19. The compound according to claim 18, wherein $R^1$ is selected from the group consisting of —CH$_2$CH=CH; —CH$_2$(3-iodophenyl); —CH$_2$CH=CH(3-quinolyl); and —CH$_2$(4-phenylphenyl).

20. The compound according to claim 18, wherein $R^2$ is —CH$_2$CO(piperizine-N-phenyl).

* * * * *

UNITED STATES PATENT AND TRADEMARK OFFICE
CERTIFICATE OF CORRECTION

PATENT NO. : 6,946,446 B2 Page 1 of 1
DATED : September 20, 2004
INVENTOR(S) : Zhenkun Ma et al.

It is certified that error appears in the above-identified patent and that said Letters Patent is hereby corrected as shown below:

Column 31,
Line 25, replace " 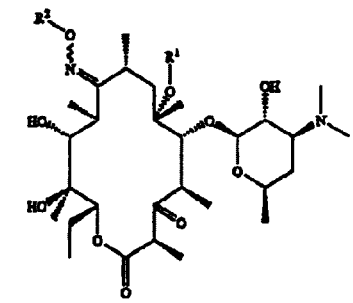 " with -- 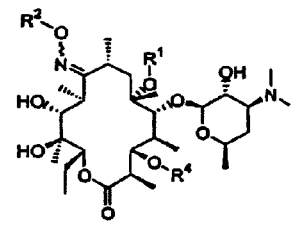 --.

Signed and Sealed this

Twenty-third Day of May, 2006

JON W. DUDAS
*Director of the United States Patent and Trademark Office*

UNITED STATES PATENT AND TRADEMARK OFFICE
CERTIFICATE OF CORRECTION

PATENT NO.     : 6,946,446 B2
DATED          : September 20, 2005
INVENTOR(S)    : Zhenkun Ma et al.

It is certified that error appears in the above-identified patent and that said Letters Patent is hereby corrected as shown below:

<u>Column 31,</u>
Line 25, replace " 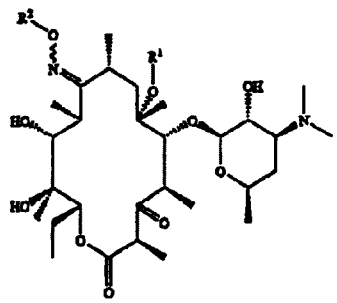 " with -- 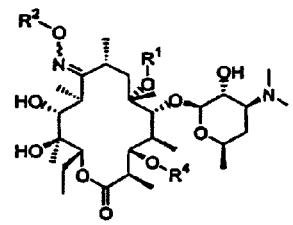 --.

This certificate supersedes Certificate of Correction issued May 23, 2006.

Signed and Sealed this

Thirteenth Day of June, 2006

JON W. DUDAS
*Director of the United States Patent and Trademark Office*